United States Patent [19]
Arana

[11] Patent Number: 4,784,134
[45] Date of Patent: Nov. 15, 1988

[54] BIOPSY LOCATOR PLATE

[76] Inventor: Thomas Arana, 89 Bloomfield St., Lexington, Mass. 02173

[21] Appl. No.: 96,153

[22] Filed: Sep. 14, 1987

Related U.S. Application Data

[62] Division of Ser. No. 930,918, Nov. 17, 1986.

[51] Int. Cl.$^4$ ............................................. A61B 17/00
[52] U.S. Cl. ................................. 128/303 R; 128/749
[58] Field of Search .............................. 128/749–759, 128/303 R, 664, 665, 754, 771, 774; 33/23.11; 83/565, 829; 132/88.5; 378/180; 101/112; 408/97, 115 B, 115 R, 72 B, 72 R

[56] References Cited

U.S. PATENT DOCUMENTS

| | | | |
|---|---|---|---|
| 2,733,517 | 2/1956 | Gjersoe | 101/112 |
| 4,306,823 | 12/1981 | Nashlund | 408/26 |
| 4,325,373 | 4/1982 | Slivenko et al. | 128/303 R |
| 4,427,005 | 1/1984 | Tener | 128/303 R |
| 4,563,768 | 1/1986 | Read et al. | 128/754 |
| 4,599,738 | 7/1986 | Panetta et al. | 378/37 |

FOREIGN PATENT DOCUMENTS 0933288  6/1982  U.S.S.R. .......................... 408/115 R

Primary Examiner—Max Hindenburg
Attorney, Agent, or Firm—Joseph S. Iandiorio; Douglas E. Denninger

[57] ABSTRACT

An adjustable biopsy paddle for compressing tissue to be examined and assisting localization of a needle relative to a nonpalpable lesion, the paddle including a locator plate having a plurality of tissue access holes of generally uniform diameter and of generally uniform spacing in a first direction, typically the lateral direction. The paddle further includes a guide for permitting movement of the plate in the first direction for a distance of at least half the distance of the spacing, and a bracket for slidably supporting the plate.

4 Claims, 4 Drawing Sheets

BIOPSY LOCATOR PLATE

This is a division of application Ser. No. 930,918, filed Nov. 17, 1986.

This invention relates to a biopsy paddle having a plate which is adjustable in position and more particularly to a compression biopsy paddle for facile needle localization of nonpalpable breast masses.

FIELD OF INVENTION

BACKGROUND OF INVENTION

Identifying and appropriately demarcating subsurface nonpalpable lesions in tissue presents a number of difficulties for radiologists. Unless the lesion is properly localized, that is, limited or restricted to a definite area or region, the surgeon may remove an unnecessarily large amount of tissue or may inadvertently leave a portion or all of the lesion unexcised.

Nonpalpable breast masses are presently localized using a compression biopsy paddle. The biopsy paddle, such as incorporated in the Phillips Mammographic System available from Phillips, Netherlands, has a locator plate which is rigidly and permanently held by a bracket that in turn mounts to a support which permits the paddle to be raised and lowered. The locator plate has a number of access holes distributed across the plate and arranged in rows and columns. To localize a lesion, the breast is placed on a cassette containing X-ray film and positioned to place the lesion close to the upper surface. The biopsy paddle is lowered to compress the breast and the X-ray film is exposed by passing radiation through the locator plate, which is radiotranslucent The lesion is located on the film and the radiologist then must insert a localization needle through an access hole of the locator plate into the breast and into the lesion. However, the access holes are separated by intervals of solid material. When a small lesion lies beneath an interval rather than an access hole, the biopsy paddle must be elevated and the patient's breast physically moved either medially or laterally to attempt to bring the lesion beneath an access hole. Moving the patient physically over the cassette is difficult, especially if the patient is sweating, and moving the patient only a small amount is particularly difficult. Further, physically moving the breast further agitates an already apprehensive patient.

After adjustment of the breast the biopsy paddle is lowered to again compress the breast and another X-ray exposure is taken. If the lesion still does not sufficiently underlie one of the access holes, the cumbersome adjustment procedure must be repeated. Once the lesion is properly positioned relative to an access hole, the needle is inserted and another X-ray film is exposed to record the position of the needle relative to the lesion. Finally, after reorienting the breast 90° and repositioning the biopsy paddle, an additional X-ray film exposure is taken perpendicular to the previous X-ray exposure to locate the needle in three dimensions relative to the lesion.

Contamination problems are also present in the above system. Since the locator plate is permanently attached to the surrounding bracket, the system is unsuited for gas sterilization Truly effective sterilization of a plastic instrument is provided by exposure to ethylene oxide. After this exposure, the instrument must stand for at least seven days to insure that the toxic gas has fully left the paddle. Presently, the paddles are simply swabbed with alcohol. But blood, sweat and other bodily fluids which contact the plate are best neutralized through gas sterilization.

SUMMARY OF INVENTION

It is therefore an object of this invention to provide an adjustable biopsy paddle which enables more accurate positioning of a locator plate over a nonpalpable lesion to be localized.

It is a further object of this invention to provide such a biopsy paddle which is easier to use.

It is a further object of this invention to provide such a biopsy paddle which engenders procedures less disturbing to the patient.

It is yet another object of this invention to provide such a biopsy paddle which has a localizor plate removable for sterilization.

It is a further object of this invention to provide such a biopsy paddle which is compatible with existing support equipment.

This invention features an adjustable biopsy paddle for compressing tissue to be examined and assisting localization of a needle relative to a nonpalpable lesion. There is a locator plate having a plurality of tissue access holes of generally uniform diameter and of generally uniform lateral spacing. There are also guide means for permitting lateral movement of the plate for a distance of at least half the distance of the spacing, and a bracket for laterally slidably supporting the plate.

In one embodiment, the guide means permits lateral movement of at least half the distance of the spacing plus half the diameter of one of the holes. The holes are generally uniformly spaced in the front-to-back direction; the inward hole spacing may be different from that of the lateral hole spacing. The bracket is U-shaped and the guide means includes means for constraining movement of the plate along the lateral direction. The guide means includes a slot in the plate and includes means for removably interlocking with the plate. The paddle may further include means for releasably engaging the bracket and plate to prevent relative movement This invention further features an adjustable biopsy paddle having a locator plate with a plurality of tissue access holes of generally uniform diameter and of generally uniform spacing along a first direction, and guide means for permitting movement of the plate along the first direction for a distance of at least half the distance of the spacing plus half the diameter of a hole. There is also a bracket for supporting the plate slidably along the first direction and means for releasably engaging the bracket and plate to prevent relative movement.

This invention also features a locator plate for use with a bracket having a recess for slidably receiving the plate to form a biopsy paddle. The plate includes a plurality of tissue access holes of generally uniform diameter and generally uniform spacing along a first direction, the plate also including guide means for permitting movement of the plate in the first direction for a distance of at least half the distance of the spacing plus half the distance of a hole.

The guide means of the locator plate may include a slot disposed proximate its rear edge and oriented along the first direction. The plate may have a thickened rim and the guide means may be disposed in a portion of the rim. The first direction may be the lateral direction.

DISCLOSURE OF PREFERRED EMBODIMENT

Other objects, features and advantages will occur from the following description of a preferred embodiment and the accompanying drawings, in which.

Figure 1:
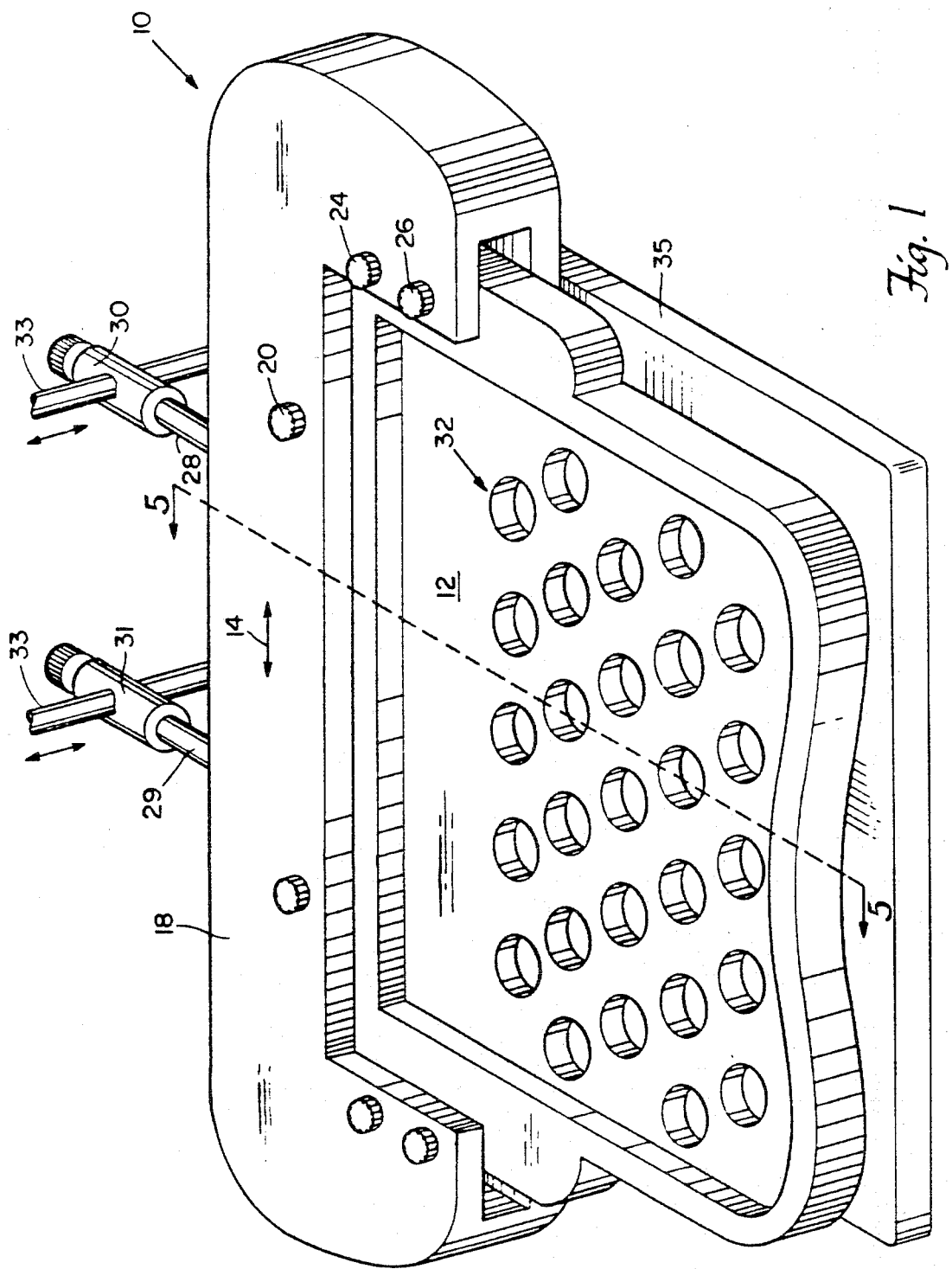
FIG. 1 is an axonometric view of a biopsy paddle according to this invention mounted in a support structure and positioned above an X-ray cassette.

This invention may be accomplished by a biopsy paddle having a locator plate which is movable within a support bracket in a first direction, typically the lateral or side-to-side direction. Movement of the plate is guided by a device such as a slot in the plate. The biopsy paddle may include an element for releasably engaging the plate and the support bracket to prevent relative movement except during adjustment of the location of the plate in relation to a lesion to h=localized Biopsy paddle 10, FIGS. 1 and 2, includes locator plate 12 which is movable only in the lateral direction, indicated by direction arrow 14 The lateral movement is guided by slot 16 on one side of plate 12 and a matching slot on the other side of paddle 12 (not shown).

Figure 2:
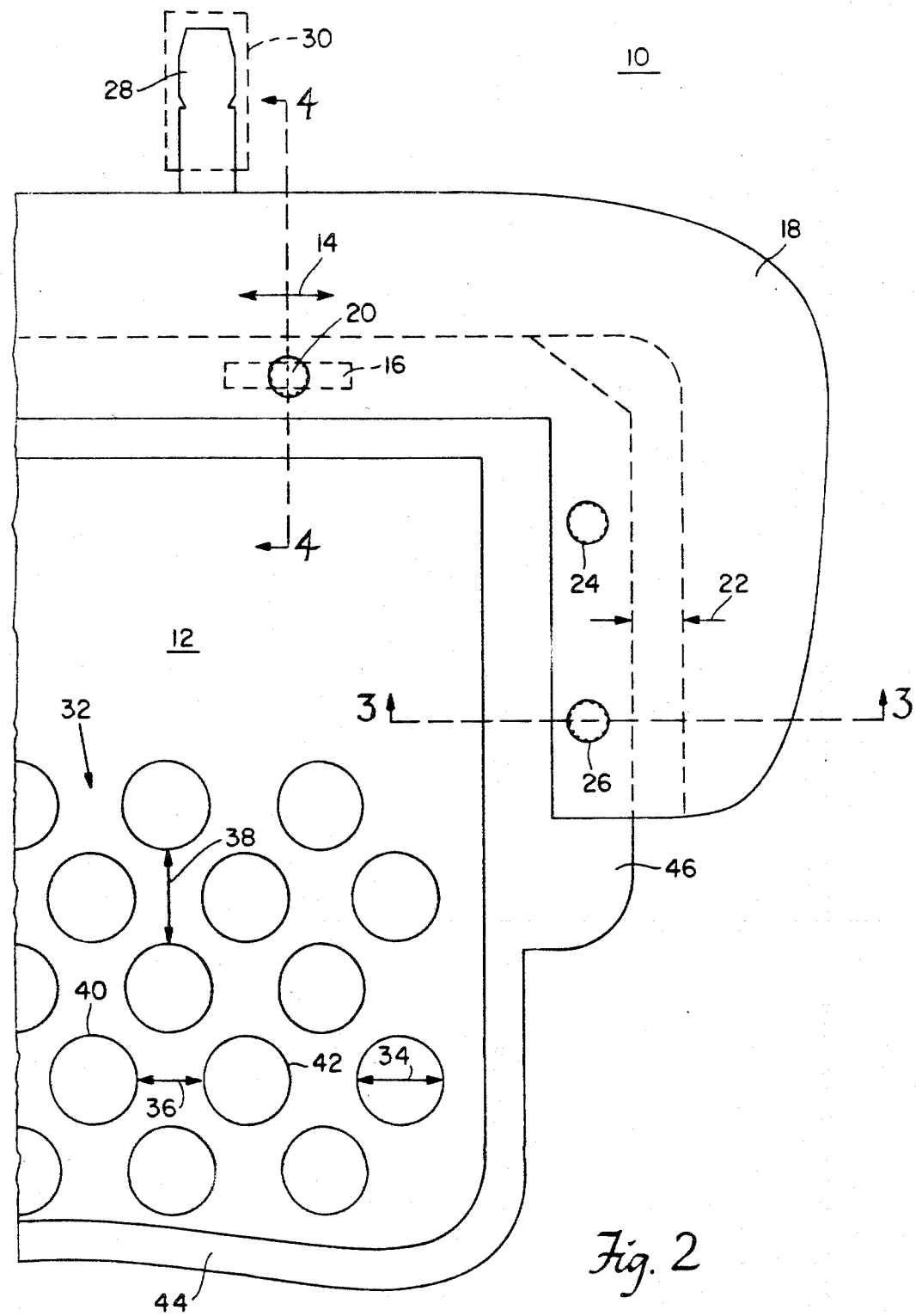
FIG. 2 is a top plan view of a section of the adjustable biopsy paddle of FIG. 1.

Slot 16 is shown in phantom in FIG. 2 as viewed through bracket 18. Set screw 20 projects into slot 16 to allow movement in the direction indicated by arrow 14 but to prevent front-to-back or rotary motion of plate 12.

Bracket 18 accommodates lateral movement of plate 12 within lateral space indicated by arrows 22. The set screws 24, 26 releasably engage plate 12 to allow lateral adjustment of plate 12 and then to arrest travel between adjustments.

Bracket 18 also includes conventional mounting posts 28 and 29, FIG. 1. Posts 28 and 29 are received by sockets 30, 31, respectively, of conventional support structure 33 such as in the Phillips Mamographic System which permits raising and lowering of biopsy paddle 10 relative to cassette 35. Posts 28, 29 are rigidly held in sockets 30, 31 to prevent all other movement.

Figure 3:
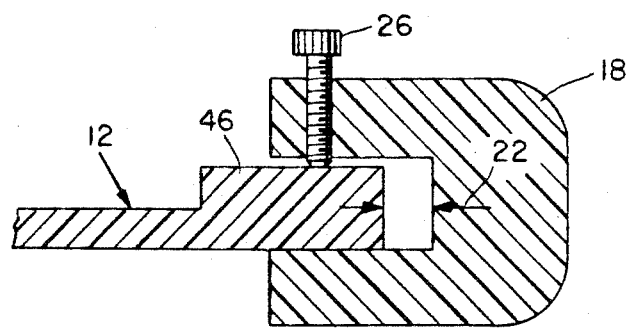
FIG. 3 is a partial cross-sectional view along lines 3—3 of FIG. 2 showing the space available for medial-lateral movement of the locator plate.

Tissue access holes 32 are of generally uniform diameter and of generally uniform spacing. Acceptable dimensions are a 19 mm diameter, indicated by arrow 34, FIG. 2, with lateral spacing of 9 mm, indicated by arrow 36, and front-to-back spacing of 17 mm, indicated by arrow 38. For these dimensions, slot 16 is at least half the length represented by arrow 36 to permit a lesion located midway between holes 40 and 42 to be accessed through a hole after lateral movement of plate 12. It is desirable for slot 16 to permit lateral movement of plate 12 not only half the distance of arrow 36—4.5 mm—but also at least half the diameter of hole 40 or 42—9.5 mm—to allow centering of the lesion beneath a tissue access hole. Slot 16 has 9 mm of play on either side of set screw 20 to readily permit centering. Structural support of plate 12 is enhanced by thickened rim 44 along the front and sides of plate 12, which broadens into thickened ridge 46 along the rear portion. Ridge 46 and bracket 18 are shown in cross section in FIG. 3, revealing gap 22 and set screw 26. Bracket 18 slidably supports ridge 46; ridge 46 lends structural strength to plate 12.

Figure 4:
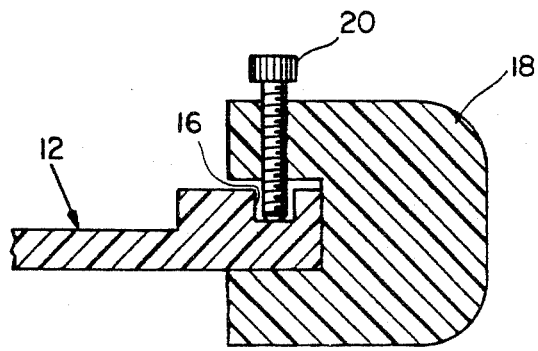
FIG. 4 is a cross-sectional view along lines 4—4 of FIG. 2 revealing one of the guide tracks in the locator plate.

Set screw 20 is shown penetrating slot 16 of plate 12 in FIG. 4. This guide assembly in combination with a matching guide assembly for the other side of biopsy paddle 10 ensures that plate 12 will not wander in an unknown direction but instead moves in a predicted manner to allow accurate positioning of plate 12 relative to a lesion to be localized. Set screw 20 is removable from its interlocking relationship with slot 16 to permit plate 12 to be removed for gas sterilization or other treatment before and after use. In a more elaborate construction a worm drive, rack-and-pinion gears, or other gear arrangement may be utilized to incrementally move plate 12.

Figure 5:
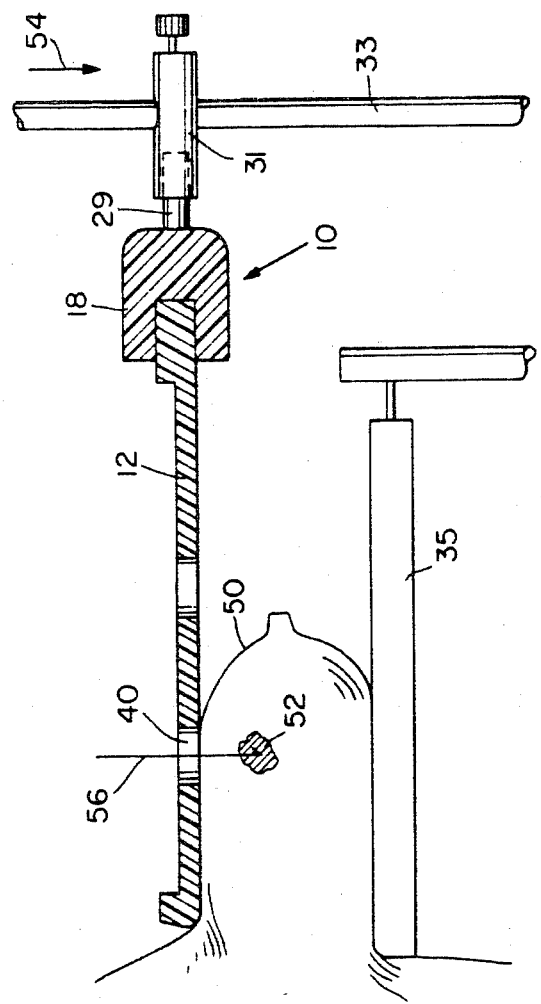
FIG. 5 is a cross-sectional view along lines 5—5 of FIG. 1 showing compression of a breast and needle localization of a lesion.

Biopsy paddle 10 is depicted in use in FIG. 5. Breast 50 is positioned on cassette 35 to place lesion 52 close to plate 12. Paddle 10 is lowered in the direction indicated by arrow 54 to compress breast 50. X-ray film in cassette 35 is exposed to determine the location of the lesion relative to hole 40. If the lesion is not accessible through hole 40, paddle 10 is raised slightly, the set screws are loosened, and plate 12 is easily shifted laterally to position hole 40 above lesion 52. Needle 56 is then inserted and its position verified as described in the Background.

Although the biopsy paddle is described above as movable in a single, lateral direction, this is not a limitation of the invention. In other constructions, a biopsy paddle according to this invention is movable diagonally or toward-and-away from a patient. Further, the biopsy paddle can move in multiple directions when the slots or other guides on the paddle extend in more than one direction.

Although specific features of the invention are shown in some drawings and not others, this is for convenience only as each feature may be combined with any or all of the other features in accordance with the invention.

Other embodiments will occur to those skilled in the art and are within the following claims

What is claimed is:

1. A locator plate for use with a bracket having a recess for slidably receiving the plate to form a biopsy paddle, said plate including a plurality of tissue access holes of generally uniform diameter and of generally uniform spacing along a first direction and arranged in a plurality of rows generally uniformly spaced in a second direction, said plate also including guide means including at least one elongated slot located in the rim of said locator plate and aligned longitudinally in said first direction to allow said plate to permit movement in said first direction up to a distance equal to at least one-half the distance of the interhole spacing plus one-half the diameter of a tissue access hole.

2. The locator plate of claim 1 in which said plate has a thickened rim.

3. The locator plate of claim 1 in which said first direction is the lateral direction.

4. The locator plate of claim 1 in which said guide means includes two elongated slots located in the rim of said plate and aligned longitudinally in said first direction to allow said plate to permit movement in said first direction up to a distance equal to at least one-half the distance of the interhole spacing plus one-half the diameter of a tissue access hole.

* * * * *